US012616684B2

(12) United States Patent
Moon et al.

(10) Patent No.: US 12,616,684 B2
(45) Date of Patent: May 5, 2026

(54) PULMONARY FIBROSIS MEDICINE CONTAINING PYRAZOLE DERIVATIVE

(71) Applicant: APTABIO THERAPEUTICS INC., Yongin-si (KR)

(72) Inventors: Sung Hwan Moon, Suwon-si (KR); Soo Jin Lee, Suwon-si (KR); Hyunkyung Yu, Suwon-si (KR); Yoo-Kyung Goh, Suwon-si (KR)

(73) Assignee: APTABIO THERAPEUTICS INC., Yongin-si (KR)

( * ) Notice: Subject to any disclaimer, the term of this patent is extended or adjusted under 35 U.S.C. 154(b) by 745 days.

(21) Appl. No.: 17/918,497

(22) PCT Filed: Mar. 23, 2021

(86) PCT No.: PCT/KR2021/003537

§ 371 (c)(1),
(2) Date: Oct. 12, 2022

(87) PCT Pub. No.: WO2021/210799

PCT Pub. Date: Oct. 21, 2021

(65) Prior Publication Data

US 2023/0148365 A1 May 11, 2023

(30) Foreign Application Priority Data

Apr. 13, 2020 (KR) ........................ 10-2020-0044598
Mar. 22, 2021 (KR) ........................ 10-2021-0036863

(51) Int. Cl.
*A61P 43/00* (2006.01)
*A61K 31/4439* (2006.01)
*A61K 45/06* (2006.01)
*A61P 11/00* (2006.01)
*A61P 31/14* (2006.01)

(52) U.S. Cl.
CPC .......... *A61K 31/4439* (2013.01); *A61K 45/06* (2013.01); *A61P 11/00* (2018.01); *A61P 31/14* (2018.01)

(58) Field of Classification Search
None
See application file for complete search history.

(56) References Cited

U.S. PATENT DOCUMENTS 10,047,067 B2 8/2018 Bae et al.
10,966,969 B2 * 4/2021 Moon ........................ A61P 1/16
11,174,240 B2 * 11/2021 Moon ...................... A61P 19/10
11,787,785 B2 10/2023 Bonazzi et al.
2011/0044981 A1 2/2011 Spangler et al.
2014/0066404 A1 3/2014 Bae et al.
2015/0218125 A1 8/2015 Bae et al.
2017/0216332 A1 8/2017 Phipps et al.
2019/0038655 A1 2/2019 Cardelli et al.
2020/0206169 A1 7/2020 Walczak et al.
2020/0390752 A1 12/2020 Moon et al.
2021/0122726 A1 4/2021 Moon et al.
2021/0275504 A1 9/2021 Foucart et al.
2023/0201179 A1 6/2023 Lee et al.

FOREIGN PATENT DOCUMENTS

CL 202202641 6/2023
CL 202302726 4/2024
CN 104755077 A 7/2015
CN 109912600 A 6/2019
CN 110248659 A 9/2019
CN 110678455 A 1/2020
EP 3613733 A1 * 2/2020 ......... A61K 31/4439
EP 3 628 669 A1 4/2020
KR 10-2004-0094464 A 11/2004
KR 10-2013-0010708 A 1/2013
KR 101280160 B1 * 6/2013
KR 10-2014-0027833 A 3/2014
KR 10-1821593 B1 1/2018
KR 10-1840702 B1 3/2018
KR 10-2019-0122806 A 10/2019
KR 10-2019-0136079 A 12/2019
RU 2 561 672 C2 8/2015
WO 2017/192304 A1 11/2017
WO 2019/088444 A1 5/2019
WO WO-2021263281 A2 * 12/2021 ............. A61K 31/05

OTHER PUBLICATIONS

Cleveland Clinic Pulmonary Fibrosis (Year: 2025).*
BetterHealth Infections bacterial and viral (Year: 2024).*
Hong et al., APX-115A, a pan-NADPH Oxidase Inhibitor, Induces Caspase-dependent Cell Deathby Suppressing NOX4-ROS Signaling in EBV-infected Retinal Epithelial Cells, Current Eye Research2020, vol. 45, No. 9, 1136â1143, Published online: Feb. 4, 2020 (Year: 2020).*
Scifinder APX-115 (Year: 2025).*
Richter et al., Reactive oxygen species and fibrosis: further evidence of a significant liaison, Cell Tissue Res (2016) 365:591-605 (Year: 2016).*
Egan et al., Viruses and idiopathic pulmonary fibrosis, Eur Respir J 1997; 10: 1433-1437 (Year: 1997).*
KR101280160B1 Translation (Year: 2013).*
Dance, Amber., Why Are There So Many Antibiotics but So Few Antiviral Drugs?, Science The Wire 2021 (Year: 2021).*
Zuo et al., SARS Coronavirus and Lung Fibrosis, S.K. Lal (ed.), Molecular Biology of the SARS-Coronavirus, DOI 10.1007/978-3-642-03683-5_15, # Springer-Verlag Berlin Heidelberg 2010 (Year: 2010).*

(Continued)

*Primary Examiner* — Kortney L. Klinkel
*Assistant Examiner* — Alison Azar Salamatian
(74) *Attorney, Agent, or Firm* — Sughrue Mion, PLLC

(57) ABSTRACT

A pharmaceutical composition or an antiviral agent for the treatment of pulmonary fibrosis is disclosed. The composition or the antiviral agent contains a compound of Formula 1, which is a pyrazole derivative, or a pharmaceutically acceptable salt thereof.

9 Claims, 9 Drawing Sheets

Specification includes a Sequence Listing.

(56) References Cited

OTHER PUBLICATIONS

Communication issued Feb. 20, 2025 in Chinese Application No. 202180028319.3.
Louise Hecker et al., "Targeting NOX enzymes in pulmonary fibrosis", Cellular and Molecular Life Sciences, 2012, vol. 69, pp. 2365-2371, Abstract Only (17 pages total).
Brian Griffith et al., "NOX Enzymes and Pulmonary Disease", Antioxidants & Redox Signaling, 2009, vol. 11, No. 10, pp. 2505-2516 (23 pages total).
Ashish Kurundkar et al. "Redox mechanisms in age-related lung fibrosis", Redox Biology, 2016, vol. 9, pp. 67-76 (10 pages total).
Gabriel Laghlali et al., "Targeting endosomal NOX2 as a potential therapy to limit influenza A virus infection", Respirology, 2019, vol. 24, Issue 10, pp. 935-936 (2 pages total).
Eunice E. To et al., "Endosomal NOX2 oxidase exacerbates virus pathogenicity and is a target for antiviral therapy", Nature communications, 2017, vol. 8, No. 69, pp. 1-17 (17 pages total).
Alessandro G. Fois et al., "Evaluation of oxidative stress biomarkers in idiopathic pulmonary fibrosis and therapeutic applications: a systematic review", Respiratory Research, 2018, vol. 19, No. 51, pp. 1-13 (13 pages total).
Eun-Mi Ha et al., "A Direct Role for Dual Oxidase in *Drosophila* Gut Immunity", Science, 2005, vol. 310, pp. 847-850 (6 pages total).
Eunice E. To et al., "Novel endosomal NOX2 oxidase inhibitor ameliorates pandemic influenza A virus-induced lung inflammation in mice", Respirology, 2019, pp. 1-7 (7 pages total).
Seung-Woo Hong et al., "APX-115A, a pan-NADPH Oxidase Inhibitor, Induces Caspase-dependent Cell Death by Suppressing NOX4-ROS Signaling in EBV-infected retinal epithelial cells", Current Eye Research, Jan. 2020, vol. 45, pp. 1136-1143 (26 pages total).
Jin Joo Cha et al., "APX-115, a first-in-class pan-NADPH oxidase (Nox) inhibitor, protects db/db mice from renal injury", Laboratory Investigation, 2017, vol. 97, No. 4, pp. 419-431 (13 pages total).
Guideock Kwon et al., "A novel pan-Nox inhibitor, APX-115, protects kidney injury in streptozotocin-induced diabetic mice: possible role of peroxisomal and mitochondrial biogenesis", Oncotarget, 2017, vol. 8, No. 43, pp. 74217-74232 (16 pages total).
Sae Rom Lee et al., "Function of NADPH Oxidases in Diabetic Nephropathy and Development of Nox Inhibitors", Biomolecules & Therapeutics, 2020, vol. 28, No. 1, pp. 25-33 (9 pages total).
Elizabeth M. Brunt et al., "The NAS and The Histopathologic Diagnosis in NAFLD: Distinct Clinicopathologic Meanings", Hepatology, 2011, vol. 53, No. 3, pp. 810-820 (24 pages total).
T Ashcroft et al., "Simple method of estimating severity of pulmonary fibrosis on a numerical scale", J Clin Pathol, 1988, vol. 41, pp. 467-470 (4 pages total).
Arka De et al., "Natural History of Simple Steatosis or Nonalcoholic Fatty Liver", Journal of Clinical and Experimental Hepatology, 2019, pp. 1-8 (9 pages total).
Frank Van Den Hoogen et al., "Classification Criteria for Systemic Sclerosis: An ACR-EULAR Collaborative Initiative", Arthritis Rheum., 2013, vol. 65, No. 11, pp. 2737-2747 (19 pages total).
International Search Report dated Jul. 19, 2021 in International Application No. PCT/KR2021/003537.
Written Opinion of the International Searching Authority dated Jul. 19, 2021 in International Application No. PCT/KR2021/003537.
Malaviya, et al., "Anti-TNFα Therapy in inflammatory lung diseases", Pharmacology & Therapeutics, 2017, vol. 180, pp. 90-98 (9 pages).
Cui, "Respiratory & Critical Care Medicine", Chinese Medical Multimedia Press, 2018-2019 (6 pages).
Hua, et al., "The Recent Progresses of Heterocyclic Compounds as Plant Virucides", Pesticides, 2002,vol. 41, No. 2 (6 pages).
European Search Report dated Apr. 17, 2024 in Application No. 21787824.8.
Chinese Office Action dated May 9, 2024 in Application No. 202180028319.3.
Russian Office Action dated Nov. 22, 2023 in RU Application No. 2022125882/04.
Zhao, et al., "Total Glucosides of Danggui Buxue Tang Attenuate BLM-Induced Pulmonary Fibrosis via Regulating Oxidative Stress by Inhibiting NOX4", Hindawi Publishing Corporation, Oxidative Medicine and Cellular Longevity, vol. 2015, Article ID 645814 (11 pages).
Dorotea, et al., "A pan-NADPH Oxidase Inhibitor Ameliorates Kidney Injury in Type 1 Diabetic Rats", Pharmacology, 2018, pp. 180-189 (10 pages).

* cited by examiner

```
                    SEQUENCE LISTING

<160> NUMBER OF SEQ ID NOS: 6

<210> SEQ ID NO 1
<211> LENGTH: 22
<212> TYPE: DNA
<213> ORGANISM: Artificial sequence
<220> FEATURE:
<223> OTHER INFORMATION: forward primer

<400> SEQUENCE: 1

ccacagacct tccaggagaa tg                                              22


<210> SEQ ID NO 2
<211> LENGTH: 23
<212> TYPE: DNA
<213> ORGANISM: Artificial sequence
<220> FEATURE:
<223> OTHER INFORMATION: reverse primer

<400> SEQUENCE: 2

gtgcagttca gtgatcgtac agg                                             23


<210> SEQ ID NO 3
<211> LENGTH: 20
<212> TYPE: DNA
<213> ORGANISM: Artificial sequence
<220> FEATURE:
<223> OTHER INFORMATION: gtggctggct cagaaaaagg

<400> SEQUENCE: 3

gtggctggct cagaaaaagg                                                 20


<210> SEQ ID NO 4
<211> LENGTH: 20
<212> TYPE: DNA
<213> ORGANISM: Artificial sequence
<220> FEATURE:
<223> OTHER INFORMATION: reverse primer

<400> SEQUENCE: 4

ggtggtccag gggtcttact                                                 20


<210> SEQ ID NO 5
<211> LENGTH: 22
<212> TYPE: DNA
<213> ORGANISM: Artificial sequence
<220> FEATURE:
```

-continued

```
<223> OTHER INFORMATION: forward primer

<400> SEQUENCE: 5

caccattggc aatgagcggt tc                                          22


<210> SEQ ID NO 6
<211> LENGTH: 22
<212> TYPE: DNA
<213> ORGANISM: Artificial sequence
<220> FEATURE:
<223> OTHER INFORMATION: reverse primer

<400> SEQUENCE: 6

aggtctttgc ggatgtccac gt                                          22
```

PULMONARY FIBROSIS MEDICINE CONTAINING PYRAZOLE DERIVATIVE

CROSS REFERENCE TO RELATED APPLICATIONS

This application is a National Stage of International Application No. PCT/KR2021/003537 filed Mar. 23, 2021, claiming priority based on Korean Patent Application No. 10-2020-0044598 filed Apr. 13, 2020 and Korean Patent Application No. 10-2021-0036863 filed Mar. 22, 2021, the disclosure of which are herein incorporated by reference in their entirety.

INCORPORATION BY REFERENCE OF SEQUENCE LISTING

The content of the electronically submitted sequence listing, file name: Q277371_SEQ_LIST_ST25.txt; size: 1,628 bytes; and date of creation: Sep. 4, 2025, is incorporated herein by reference in its entirety.

TECHNICAL FIELD

The present invention relates to a pyrazole derivative useful for preventing or treating pulmonary fibrosis, a method for preparing the same, and a pharmaceutical composition thereof.

BACKGROUND ART

Pulmonary fibrosis (PF) is a type of chronic interstitial lung disease and characterized by infiltration of inflammatory cells such as lymphocytes and macrophages into the lung interstitium, proliferation of fibroblasts, and deposition of fibrous connective tissue into the lung interstitium. Pulmonary fibrosis is caused by various internal and external etiology of the lungs, is a result of chronic lung damage or disease progressing to the end, and seriously threatens human health.

The etiology of pulmonary fibrosis includes factors such as immune dysfunction, viral or bacterial infection, drugs and chemicals, radiation, and air pollution (smog, cigarette smoke, dust, and the like).

As mentioned above, there are patients who may diagnose the clear cause of pulmonary fibrosis, but there are also cases where the cause cannot be elucidated, wherein such cases are called idiopathic pulmonary fibrosis (IPF). Idiopathic pulmonary fibrosis is a type of interstitial pneumonia in which fibrosis of the lung parenchyma is progressively progressing, and is known to have a high risk of death due to respiratory failure within a few years after diagnosis and a very poor prognosis. The 5-year survival rate is about 20%, similar to that of lung cancer. In addition, the incidence and prevalence of pulmonary fibrosis are rapidly increasing with the aging population.

Pulmonary fibrosis is a complex pathological and physiological process, wherein in the early stage, a large number of inflammatory cells infiltrate around the inflammatory site of the lung to cause the alveolar wall to become chronically thickened, and in the middle/end stage, normal lung tissue structure is destroyed due to overgrowth, alveolar deformation, hardening and scarring of the lung tissue caused by excessive deposition of extracellular matrix elements such as collagen by fibroblasts to result in loss of function.

Fibroblasts play a role in the recruitment of immune cells to sites of inflammation and tissue damage. In addition, fibroblasts produce and respond to many inflammatory cytokines. Thus, fibroblasts may contribute to chronic inflammation, and conversely, inflammatory cytokines promote the conversion of fibroblasts to myofibroblasts, thereby promoting fibrosis. Therefore, injury or inflammation of the lung tissue may lead to pulmonary fibrosis.

Lung transplantation is the only method to repair lung tissue with progressive fibrosis due to pulmonary fibrosis, and the 5-year survival rate after diagnosis is only 43%.

Although many clinical studies are being conducted to develop a therapeutic agent for pulmonary fibrosis, there is still no therapeutic agent for lung fibrosis, and immunosuppressants, which are steroids or cytotoxic drugs, are mainly used as a first-line. Among steroids and cytotoxic drugs, steroids are used first, and a combination therapy of steroids and azathioprine or cyclophosphamide is currently being used.

In addition, pirfenidone and nintedanib are the only approved drugs for the treatment of pulmonary fibrosis. It has been reported that pirfenidone has a mild therapeutic effect and is used at a very high dose of about 2.4 g/day, but there is little or no significant improvement in survival, and since it tends to decrease the quality of life of patients due to severe side effects such as gastrointestinal disorders (nausea, diarrhea, dyspepsia), skin disorders (photosensitive rash) and metabolic and nutritional disorders (anorexia, anepithymia) and weakens the liver function, continuous administration is difficult. It has been reported that nintedanib is used at a dose of 200 to 400 mg/day and reduces the incidence of acute exacerbations of mild to severe idiopathic pulmonary fibrosis, but continuous administration is difficult due to many side effects and gastrointestinal side effects.

Therefore, there is an urgent need to develop new drugs that may treat the underlying cause rather than alleviate the progression of the symptoms of a disease.

Although many studies are being conducted on the causes of pulmonary fibrosis, the pathogenesis is still unclear, making it difficult to develop therapeutic agents, but research results have been reported that oxidative stress due to the generation of excessive activated oxygen according to changes in redox homeostasis in vivo plays an important role in the progression and exacerbation of pulmonary fibrosis.

Oxidative stress refers to tissue damage caused by a relatively excessive production of reactive oxygen species as the balance between the production of reactive oxygen species (ROS) and the antioxidant defense mechanism for biomolecules, cells and tissues is broken. In particular, it has been reported that oxidative stress generated in the lung tissue induces and worsens pulmonary fibrosis. It has been reported that TGF-β stimulation in the lung tissue of patients with progressive pulmonary fibrosis induces an increase in the generation of reactive oxygen species and increases the expression of collagen and α-smooth muscle actin (α-SMA), which are important for fibrosis. In particular, it has been reported that pulmonary fibrosis worsens due to reactive oxygen species in the lung tissue of patients with idiopathic pulmonary fibrosis.

RNA virus or DNA virus infection also causes fatal lung damage through pneumonia and pulmonary fibrosis, leading to death. It has been reported that when single-stranded viruses (corona virus, influenza virus, respiratory syncytial virus, rhinovirus, dengue virus, HIV, and the like) and DNA viruses (adenovirus, vaccinia virus, herpes simplex virus, and the like) invade cells and form endosomes, reactive oxygen species are generated to promote virus replication, and the rapidly amplified virus penetrates into the lung tissue to cause lung damage while promoting inflammation and fibrosis.

Currently, in the case of viral infection, rapid amplification in the human body causes rapid lung damage, making treatment difficult, and thus, if a therapeutic agent for inhibiting the generation of reactive oxygen species and an antiviral agent are used in combination in order to treat and alleviate lung damage caused by viral infection and rapid amplification, it will be possible to more effectively treat viral pneumonia and pulmonary fibrosis. In this case, as antiviral agents that may be used in combination, representative drugs include remdesivir, ritonavir, lopinavir, favilavir, and the like.

It has been reported that TGF-β stimulation in the lung tissue of patients with progressive pulmonary fibrosis induces an increase in the generation of reactive oxygen species and increases the expression of collagen and α-smooth muscle actin (α-SMA), which are important for fibrosis, and it has been reported that pulmonary fibrosis worsens due to reactive oxygen species in the lung tissue of patients with idiopathic pulmonary fibrosis.

On the other hand, none of the prior art document discloses that the pyrazole-based compound of the present invention is effective in preventing and treating pulmonary fibrosis.

PRIOR ART DOCUMENTS (Patent Document 1) Korean Patent No. 10-1280160

(Patent Document 2) Korean Patent Application Laid-Open No. 10-2019-0122806

(Patent Document 3) Korean Patent Application Laid-Open No. 10-2019-0136079

(Non-Patent Document 1) Gabriel Laghlali, et al. Respiratory 2019, 13629.

(Non-Patent Document 3) Eunice E. To et al. Nature communications, 8(69), 1-17.

(Non-Patent Document 3) Alessandro G. Fois, Panagiotis Paligiannis et al., Respir Res. 2018, 19:51.

DISCLOSURE

Technical Problem

It is an object of the present invention to provide a pharmaceutical composition comprising a compound of Formula 1 or a pharmaceutically acceptable salt thereof.

It is another object of the present invention to provide a pharmaceutical composition for effectively inhibiting the generation of reactive oxygen species, comprising a compound of Formula 1 or a pharmaceutically acceptable salt thereof.

It is another object of the present invention to provide a pharmaceutical composition for treating or preventing pulmonary fibrosis, comprising a compound of Formula 1 or a pharmaceutically acceptable salt thereof.

It is another object of the present invention to provide a method of preventing or treating pulmonary fibrosis by administering a compound of Formula 1 or a pharmaceutically acceptable salt thereof to an individual.

It is another object of the present invention to provide the use of a compound of Formula 1 or a pharmaceutically acceptable salt thereof for preventing or treating pulmonary fibrosis.

It is another object of the present invention to provide a pharmaceutical composition for treating and preventing pulmonary fibrosis, further comprising a compound of Formula 1 or a pharmaceutically acceptable salt thereof, and an antibiotic, an antifungal agent, an antiviral agent, an anti-inflammatory agent or any combination thereof.

It is another object of the present invention to provide a method of preventing or treating pulmonary fibrosis by further administering to an individual a compound of Formula 1 or a pharmaceutically acceptable salt thereof, and an antibiotic, an antifungal agent, an antiviral agent, an anti-inflammatory agent or any combination thereof.

It is another object of the present invention to provide the use of a compound of Formula 1 or a pharmaceutically acceptable salt thereof, and an antibiotic, an antifungal agent, an antiviral agent, an anti-inflammatory agent or any combination thereof for preventing or treating pulmonary fibrosis.

It is another object of the present invention to provide an antiviral agent comprising a compound of Formula 1 or a pharmaceutically acceptable salt thereof.

It is another object of the present invention to provide a method of preventing or treating a viral disease by administering a compound of Formula 1 or a pharmaceutically acceptable salt thereof to an individual.

It is another object of the present invention to provide the use of a compound of Formula 1 or a pharmaceutically acceptable salt thereof for preventing or treating a viral disease.

Technical Solution

In order to achieve the above objects, the present invention provides a pharmaceutical composition for preventing and improving or treating pulmonary fibrosis or an viral disease, comprising a pyrazole-based compound represented by following Formula 1 or a pharmaceutically acceptable salt thereof:

Formula 1

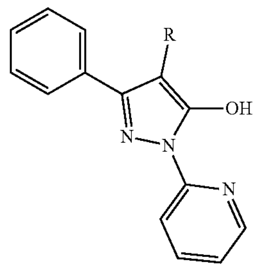

wherein R is a linear or branched alkyl group having 1 to 10 carbon atoms.

Advantageous Effects

The pyrazole-based compound according to the present invention or a pharmaceutically acceptable salt thereof may effectively inhibit the generation of reactive oxygen species generated in the lungs, and thus may be usefully used for the prevention or treatment of oxidative stress-induced pulmonary fibrosis without any particular side effects.

In addition, the pyrazole-based compound according to the present invention or a pharmaceutically acceptable salt thereof has antiviral activity, and thus may be usefully used for the prevention or treatment of a viral disease.

BEST MODE

Figure 1:
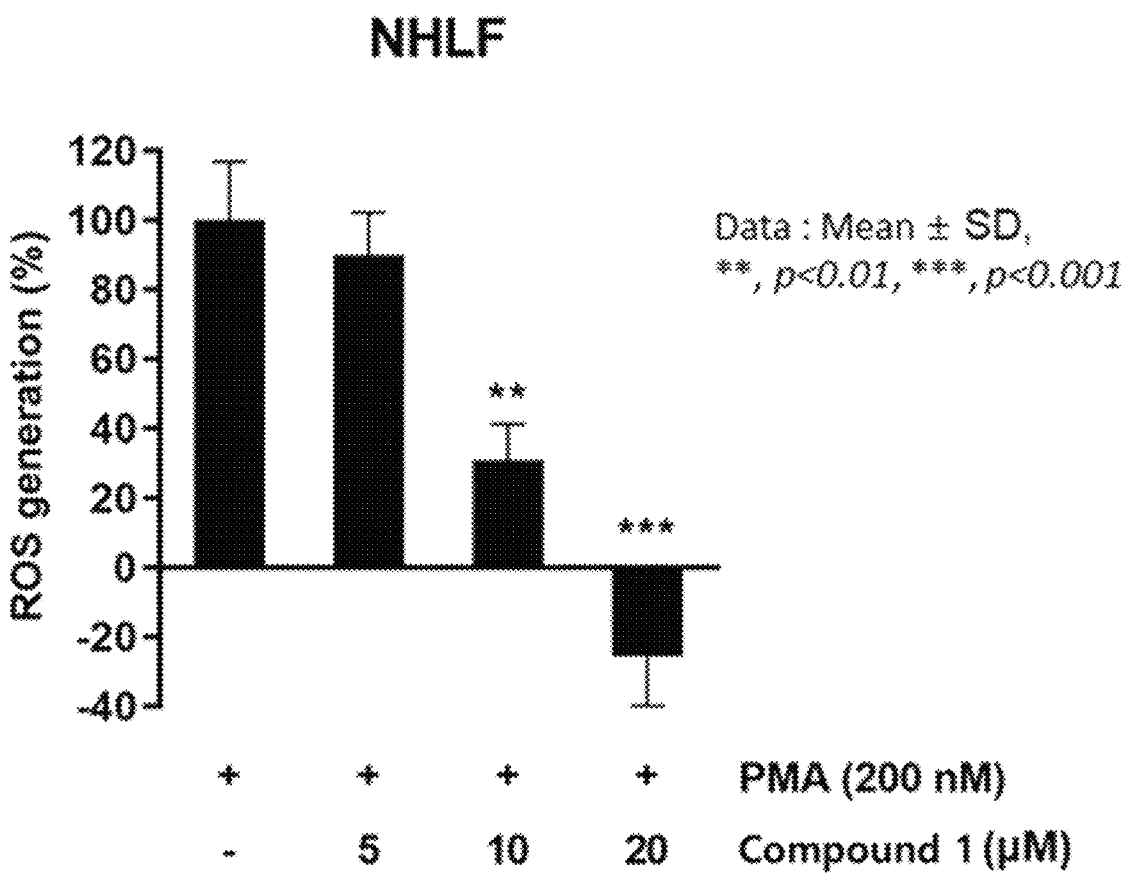
FIG. 1 shows the result of effectively inhibiting the expression of PMA stimulation-induced reactive oxygen species in normal human lung fibroblasts (NHLFs) when treated with Compound 1.

Hereinafter, the present invention will be described in more detail with reference to embodiments.

However, the present invention is not limited by the embodiments that have been represented by way of example, and the present invention is defined only by the scope of the appended claims. In addition, even if it is a constitution essential for practicing the present invention, a specific description of the constitution that may be easily practiced by the skilled artisan will be omitted.

The terms and words as used in the present specification and claims should not be construed as limited to conventional or dictionary meanings, but should be construed as the meaning and concept consistent with the technical idea of the present invention based on the principle that the inventor can appropriately define the concept of the term to describe its own invention in the best way.

The terms used in the present invention are for the purpose of describing specific embodiment only and are not intended to limit the present invention. Singular expressions include plural expressions unless the context clearly indicates otherwise. In the present invention, terms such as "comprise" and "have" are intended to indicate that there is a feature, number, step, operation, component, part, or combination thereof described in the specification, and it should be understood that the terms do not exclude in advance the possibility of the presence or addition of one or more other features, numbers, steps, operations, components, parts, or combinations thereof.

Pulmonary fibrosis is a fibrosis of the lung parenchyma caused by infiltration of inflammatory cells into the lung interstitium, proliferation of fibroblasts, and deposition of fibrous connective tissue into the lung interstitium due to inflammation of the lung, and normal lung tissue structure is destroyed to result in loss of lung function. That is, Pulmonary fibrosis is caused by various internal and external etiology of the lungs and is a result of chronic lung damage or disease progressing to the end, and the incidence and prevalence are rapidly increasing in line with the recent aging trend. Recently, in particular, idiopathic pulmonary fibrosis of unknown cause of disease has become a problem.

Lung transplantation is the only method to repair lung tissue with progressive fibrosis due to pulmonary fibrosis, and pirfenidone and nintedanib are the only approved drugs for pulmonary fibrosis, but both drugs have a problem that continuous administration is difficult due to many side effects and gastrointestinal disorders.

Therefore, a treatment method for pulmonary fibrosis is generally symptomatic therapy to relieve symptoms using steroids or immunosuppressants, but there is a need for a fundamental treatment method.

As a result of research focusing on the fact that a therapeutic agent for pulmonary fibrosis may be developed if the generation of oxidative stress in the lung tissue is effectively inhibited, the present inventors have completed the present invention by discovering that the pyrazole derivative of the present invention reduces bleomycin administration-induced lung damage and inhibits αSMA and collagen I accumulation-induced pulmonary fibrosis, thereby reducing pulmonary fibrosis, and confirming that it may be used as a therapeutic agent for pulmonary fibrosis.

Accordingly, the present invention provides a pharmaceutical composition capable of preventing or treating pulmonary fibrosis, comprising one or more compounds selected from the pyrazole-based compound represented by Formula 1 or a pharmaceutically acceptable salt thereof.

In addition, the present invention provides a pharmaceutical composition capable of preventing or treating idiopathic pulmonary fibrosis, comprising one or more compounds selected from the pyrazole-based compound represented by Formula 1 or a pharmaceutically acceptable salt thereof.

The pyrazole-based compound used in the present invention is represented by the following Formula 1:

<Formula 1>

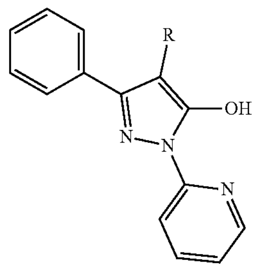

wherein R is a linear or branched alkyl group having 1 to 10 carbon atoms.

The pharmaceutically acceptable salt of the pyrazole-based compound included in the pharmaceutical composition of the present invention refers to salts that retain the biological effectiveness and properties of the parent compound and are not harmful biologically or otherwise when administered in a single dosage. In addition, it refers to a salt commonly used in the pharmaceutical industry.

Specifically, pharmaceutically acceptable addition salts may be prepared from inorganic and organic bases. Salts derived from inorganic bases may include, but are not limited to, sodium, potassium, lithium, ammonium, calcium, and magnesium salts. Salts derived from organic bases include, but are not limited to, salts of primary, secondary and tertiary amines; substituted amines including naturally occurring substituted amines; and isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamine, theobromine, purine, piperazine, piperidine, and/or cyclic amines including N-ethylpiperidine.

It should be also understood that other carboxylic acid derivatives, specifically carboxylic acid amides, including carboxamides, lower alkyl carboxamides, di(lower alkyl) carboxamides, and the like, are also useful in the practice of the present invention.

Additionally, pharmaceutically acceptable acid addition salts may be prepared from inorganic and organic acids. Salts derived from inorganic acids include hydrochloric acid, hydrobromic acid, sulfuric acid, nitric acid, phosphoric acid, perchloric acid, iodic acid, tartaric acid, and the like. Salts derived from organic acids may include, but are not limited to, acetic acid, trifluoroacetic acid, propionic acid, glycolic acid, gluconic acid, galacturonic acid, glutamic acid, glutaric acid, glucuronic acid, aspartic acid, ascorbic acid, carbonic acid, vanillic acid, hydroiodic acid, pyruvic acid, oxalic acid, malic acid, malonic acid, lactic acid, succinic acid, maleic acid, fumaric acid, tartaric acid, citric acid, benzoic acid, cinnamic acid, mandelic acid, methanesulfonic acid, ethanesulfonic acid, benzenesulfonic acid, p-toluenesulfonic acid, naphthalenesulfonic acid and/or salicylic acid, and the like.

The pharmaceutically acceptable salt may be a hydrochloride salt.

The pyrazole-based compound represented by Formula 1 or a pharmaceutically acceptable salt thereof included in the pharmaceutical composition of the present invention is specifically exemplified as follows:

3-phenyl-4-methyl-1-(pyridin-2-yl)-1H-pyrazol-5-ol or a hydrochloride salt thereof;

3-phenyl-4-ethyl-1-(pyridin-2-yl)-1H-pyrazol-5-ol or a hydrochloride salt thereof;

3-phenyl-4-n-propyl-1-(pyridin-2-yl)-1H-pyrazol-5-ol or a hydrochloride salt thereof;

3-phenyl-4-isopropyl-1-(pyridin-2-yl)-1H-pyrazol-5-ol or a hydrochloride salt thereof;

3-phenyl-4-n-butyl-1-(pyridin-2-yl)-1H-pyrazol-5-ol or a hydrochloride salt thereof;

3-phenyl-4-tert-butyl-1-(pyridin-2-yl)-1H-pyrazol-5-ol or a hydrochloride salt thereof;

3-phenyl-4-n-pentyl-1-(pyridin-2-yl)-1H-pyrazol-5-ol or a hydrochloride salt thereof;

3-phenyl-4-n-hexyl-1-(pyridin-2-yl)-1H-pyrazol-5-ol or a hydrochloride salt thereof.

Specifically, the pyrazole-based compound included in the pharmaceutical composition of the present invention may be 3-phenyl-4-n-propyl-1-(pyridin-2-yl)-1H-pyrazol-5-ol or a hydrochloride salt thereof.

The compound of Formula 1 of the present invention may inhibit the generation of reactive oxygen species.

In the present invention, oxidative stress refers to tissue damage caused by a relatively excessive production of reactive oxygen species when the balance between the production of reactive oxygen species (ROS) and the antioxidant defense mechanism for biomolecules, cells and tissues is broken. In this case, "reactive oxygen species" may refer to activated oxygen, active oxygen, and activated oxygen species, which refer to the same substance.

The pyrazole-based compound of the present invention, in particular, the hydrochloride salt of 3-phenyl-4-n-propyl-1-(pyridin-2-yl)-1H-pyrazol-5-ol (Compound 1) effectively reduced reactive oxygen species in human lung epithelial cells, and effectively inhibited the expression of αSMA and collagen I, which are myofibroblast differentiation markers, when lung fibroblasts were differentiated into myofibroblasts.

In addition, as confirmed by experiments in animal models with bleomycin-administered pulmonary fibrosis, the compound of the present invention reduced the infiltration of inflammatory cells into the lung tissue, decreased lung epithelial cell hypertrophy, reduced deformation of the lung structure, and reduced the site of abnormal tissue deposition, compared to nintedanib, which was approved as a conventional therapeutic agent for pulmonary fibrosis.

The compound of the present invention decreased the expression and accumulation of collagen I and αSMA in the lung tissue, and also decreased the expression of reactive oxygen species in the lung tissue, compared to nintedanib. Based on these results, when the severity of fibrosis was quantified with the improved Ashcroft scale, it showed a remarkable improvement effect in pulmonary fibrosis compared to nintenadib, which was approved as a conventional therapeutic agent for pulmonary fibrosis.

Therefore, it was confirmed that the compound of the present invention not only suppresses the inflammatory response by inhibiting reactive oxygen species in the lung tissue in human lung cells and lung fibrosis models, but also prevents or alleviates pulmonary fibrosis by reducing the expression and accumulation of collagen I and αSMA.

The pulmonary fibrosis may be caused by pulmonary inflammatory fibrosis, chronic obstructive pulmonary disease (COPD) combined pulmonary fibrosis, idiopathic pulmonary fibrosis (IPF) or asthma.

In addition, the pneumonia, which may be said to be the main cause of pulmonary fibrosis, may be caused by viral pneumonia, bacterial pneumonia, fungal pneumonia, hypersensitivity pneumonitis, aspiration pneumonia, interstitial pulmonary disease, pneumoconiosis, and the like.

The viral pneumonia may be caused by a virus selected from adenovirus, vaccinia virus, herpes simplex virus, parainfluenza virus, rhinovirus, varicella zoster virus, measle virus, respiratory syncytial virus, dengue virus, human immunodeficiency virus (HIV), influenza virus, coronavirus, severe acute respiratory syndrome-related coronavirus (SARS-CoV), severe acute respiratory syndrome-related coronavirus 2 (SARS-CoV2), middle east respiratory syndrome coronavirus (MERS-CoV), or variant viruses of these viruses.

The pharmaceutical composition of the present invention may further comprise an antibiotic, an antifungal agent, an antiviral agent, an anti-inflammatory agent or any combination thereof as a second therapeutic agent, in addition to the compound of Formula 1 or a salt thereof.

Specifically, the antibiotic included in the second therapeutic agent is gentamycin, kanamycin, streptomycin, amikacin, neomycin, and the like, among aminoglycoside antibiotics; erythromycin, azithromycin, clarithromycin, and the like, among macrolide antibiotics; penicillin, cephalosporin, carbapenem, monobactam, and the like, among the beta-lactam antibiotics; clindamycin, and the like, as lincomycin antibiotics; linezolid, and the like, as oxazolidinone antibiotics; ciprofloxacin, lebofloxacin, moxifloxacin, fluoroquinolone, and the like, as a quinolone antibiotic; tetracycline, doxycycline, tigecycline, and the like, as tetracycline antibiotics; trimethoprime/sulfamethoxazole (TMX/SMX), as sulfonamide antibiotics; or a combination thereof.

The antiviral agent included in the second therapeutic agent is thiosemicarbazone, metisazone, acyclovir, remdecivir, ritonavir, lopinavir, faviravir, idoxuridine, vidarabine, ribavirin, ganciclovir, famciclovir, valaciclovir, cidofovir, valganciclovir, brivudine, ribavirin, rimantadine, tromantadine, foscarnet, saquinavir, indinavir, nelfinavir, amprenavir, fosamprenavir, atazanavir, tipranavir, zidovudine, didanosine, zalcitabine, stavudine, lamivudine, abacavir, tenofovir disoproxil, adefovir disoproxil, emtricitabine, entecavir, nevirapine, delavirdine, efavirenz, zanamivir, oseltamivir, inosine pranobex, pleconaril, enfuvirtide, or a combination thereof.

The antifungal agent included in the second therapeutic agent is allylamine, terbinafine, 5-fluoro cytosine, fluconazole, itraconazole, ketoconazole, ravuconazole, posaconazole, voriconazole, caspofungin, micafungin, anidulafungin, amphotericin B, amphotericin B lipid complex (ABLC), amphotericin B colloidal dispersion (ABCD), liposome-amphotericin B (L-AMB), liposome nystatin, griseofulvin, or a combination thereof.

The compound of Formula 1 of the present invention has antiviral activity against various viruses, and thus, the compound of the present invention may be itself used as an antiviral agent. Accordingly, the compound of Formula 1 of the present invention may be effective in preventing or treating a viral disease. The viral disease may be caused by a virus selected from, but is not limited to, adenovirus, vaccinia virus, herpes simplex virus, parainfluenza virus, rhinovirus, varicella zoster virus, measle virus, respiratory syncytial virus, dengue virus, human immunodeficiency virus (HIV), influenza virus, coronavirus, severe acute respiratory syndrome coronavirus (SARS-CoV), severe acute respiratory syndrome-related coronavirus 2 (SARS-CoV2), middle east respiratory syndrome coronavirus (MERS-CoV), or variant viruses of these viruses. In particular, the compound 1 of the present invention may effectively inhibit the proliferation of severe acute respiratory syndrome-related coronavirus 2 (SARS-CoV2), and thus may also inhibit the proliferation of its related viruses, SARS-CoV, MERS-CoV, or variant viruses of these coronaviruses.

The pharmaceutical composition of the present invention may comprise a pharmaceutically acceptable carrier within a range that does not impair the effects of the present invention.

The "pharmaceutically acceptable carrier" includes any and all kinds of solvents, dispersion media, coatings, surfactants, antioxidants, preservatives (antibacterial or antifungal agents), isotonic agents, diluents, absorption delaying agents, salts, preservatives, stabilizers, binders, excipients, disintegrants, lubricants, sweetening agents, flavouring agents, dyes, and the like, and combinations thereof, as known to those skilled in the art. Except that any conventional carrier is not compatible with the active ingredient, its use in therapeutic or pharmaceutical compositions is contemplated.

The diluent may be selected from the group consisting of, but is not limited to, microcrystalline cellulose, lactose monohydrate, lactose anhydride, lactose, starch, mannitol, carboxymethylcellulose, sorbitol, and combinations thereof.

The disintegrant may be selected from the group consisting of, but is not limited to, low-substituted hydroxypropyl cellulose, crospovidone, croscarmellose sodium, sodium starch glycolate, F-melt, and combinations thereof.

The binder may be selected from the group consisting of, but is not limited to, hydroxypropyl cellulose, hydroxypropyl methylcellulose, hypromellose, polyvinyl acetic acid, povidone, polyvinylpyrrolidone, copovidone, macrogol, sodium lauryl sulfate, light anhydrous silicic acid, synthetic aluminum silicate, silicate derivatives such as calcium silicate or magnesium metasilicate aluminate, phosphates such as calcium hydrogen phosphate, carbonates such as calcium carbonate, pregelatinized starches, gums such as acacia gum, gelatin, cellulose derivatives such as ethyl cellulose, and mixtures thereof.

The lubricant may be selected from the group consisting of, but is not limited to, magnesium stearate, silicon dioxide, talc, light anhydrous silicic acid, sodium stearyl fumarate, and combinations thereof.

As a pH adjusting agent, an acidifying agent such as acetic acid, adipic acid, ascorbic acid, sodium ascorbate, sodium etherate, malic acid, succinic acid, tartaric acid, fumaric acid and citric acid, and a basifying agent such as aqueous ammonia, sodium carbonate, magnesium oxide, magnesium carbonate, sodium citrate and tribasic calcium phosphate may be used.

As the antioxidant, dibutyl hydroxy toluene, butylated hydroxyanisole, tocopherol acetate, tocopherol, propyl gallate, sodium hydrogen sulfite, sodium pyrosulfite and the like may be used.

In addition, it is possible to formulate the agents of the present invention by selectively using various additives selected from colorants and flavourings as pharmaceutically acceptable additives.

In the present invention, the scope of the additives is not limited to using the additives, and it may be formulated to selectively contain a dose within a normal range using the additives.

The pharmaceutical composition according to the present invention may be formulated and used in the form of oral formulations such as powders, granules, tablets, capsules, suspensions, emulsions, syrups and aerosols, external preparations, suppositories, or sterile injectable solutions.

In one aspect of the present invention, it may be a pharmaceutical composition for preventing, improving or treating pulmonary fibrosis, comprising the active ingredient in the range of 0.00001 to 100% by weight, 0.0001 to 95% by weight, or 0.001 to 90% by weight based on the total weight of the pharmaceutical composition.

In the preventive or therapeutic agent for pulmonary fibrosis according to the present invention, the dosage of the pyrazole-based compound represented by Formula 1 or a pharmaceutically acceptable salt thereof may be appropriately changed depending on the age of the patient, the body weight, the symptom, the route of administration, and the like.

The dosage of the pyrazole-based compound represented by Formula 1 or a pharmaceutically acceptable salt thereof of the present invention may be 0.00001 mg/kg/day to 2000 mg/kg/day, 0.0001 mg/kg/day to 1000 mg/kg/day, 0.001 mg/kg/day to 800 mg/kg/day, 0.001 mg/kg/day to 500 mg/kg/day, 0.001 mg/kg/day to 100 mg/kg/day, 0.001 mg/kg/day to 80 mg/kg/day, or 0.01 mg/kg/day to 70 mg/kg/day.

The content of the pyrazole-based compound represented by Formula 1 or a pharmaceutically acceptable salt thereof of the present invention may be 0.00001 to 100% by weight, 0.0001 to 95% by weight, 0.0001 to 90% by weight, 0.001 to 70% by weight, or 0.001 to 50% by weight per unit dosage form.

The administration concentration of the pyrazole-based compound represented by Formula 1 or a pharmaceutically acceptable salt thereof of the present invention may be 0.0001 to 500 μM, 0.001 to 300 μM, 0.001 to 150 μM, 0.001 to 130 μM, 0.001 to 100 μM, 0.001 to 80 μM, or 0.01 to 70 μM.

The pharmaceutical composition of the present invention may be administered through a general route, and may be specifically formulated for intramuscular, intrathecal, intradigestive, intracardiovascular, intrarenal, or intravenous administration. Formulation methods employ conventional methods known to those skilled in the art.

A conventional composition for intramuscular or intrathecal administration may consist of, but not limited to, for example, the active ingredient and a sterile isotonic aqueous solution containing dextrose, sodium chloride, or both dextrose and sodium chloride. Other examples include, but are not limited to, lactated Ringer's injection, lactated Ringer's injection+dextrose injection, Normosol-M and dextrose, Isolyte E, acylated Ringer's injection, and the like. Optionally, the present formulation may comprise, but is not limited to, a cosolvent such as polyethylene glycol; chelating agents such as ethylenediamine tetraacetic acid; and antioxidants such as sodium metabisulphite. Optionally, without limitation, the solution may be lyophilized and then reconstituted with a suitable solvent immediately prior to administration.

Preferred examples are provided to help understanding of the present invention. The following examples are provided not to limit the present invention but to facilitate the understanding of the present invention.

MODE FOR CARRYING OUT THE INVENTION

<Synthetic Example 1> Synthesis of 3-phenyl-4-ethyl-1-(pyridin-2-yl)-1H-pyrazol-5-ol

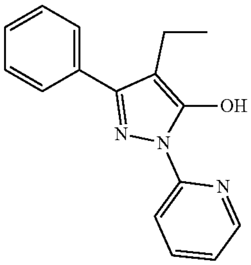 [SMILES: CCc1c(-c2ccccc2)nn(-c2ccccn2)c1O]

In a round bottom flask, 2-ethyl-3-oxo-3-phenylpropionic acid ethyl ester (10.7 g, 49 mmol) and 2-hydrazinopyridine (5.6 g, 51.4 mmol) were heated to reflux under nitrogen condition without a solvent for 1 day. The resulting solid was purified with hexane and ethyl acetate and then dried under vacuum to obtain the title compound in a yield of 70%.

1H NMR (300 MHz, DMSO-d6) δ 8.25-8.24 (1H, d), 8.00-7.97 (1H, d), 7.84-7.82 (1H, t), 7.73-7.71 (2H, m), 7.46-7.37 (3H, m) 7.12-7.11 (1H, t), 2.62-2.57 (2H, m), 1.23-1.17 (3H, m); ESI (m/z) 266.1[M+H]$^+$.

<Synthetic Example 2> Synthesis of 3-phenyl-4-butyl-1-(pyridin-2-yl)-1H-pyrazol-5-ol

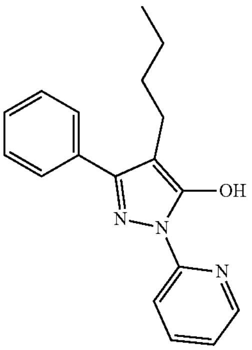 [SMILES: CCCCc1c(-c2ccccc2)nn(-c2ccccn2)c1O]

In a round bottom flask, 2-butyl-3-oxo-3-phenylpropionic acid ethyl ester (12.1 g, 49 mmol) and 2-hydrazinopyridine (5.6 g, 51.4 mmol) were heated to reflux under nitrogen condition without a solvent for 1 day. The resulting solid was purified with hexane and ethyl acetate and then dried under vacuum to obtain the title compound in a yield of 75%.

1H NMR (300 MHz, DMSO-d6) δ 8.25-8.24 (1H, d), 8.03-8.02 (1H, d), 7.85-7.83 (1H, t), 7.70-7.69 (2H, m), 7.44-7.35 (3H, m) 7.12-7.11 (1H, t), 2.56-2.53 (2H, t), 1.58-1.52 (2H, m), 1.38-1.24 (2H, m), 0.89-0.86 (3H, t); ESI (m/z) 294.0[M+H]$^+$.

<Synthetic Example 3> Synthesis of 3-phenyl-4-propyl-1-(pyridin-2-yl)-1H-pyrazol-5-ol

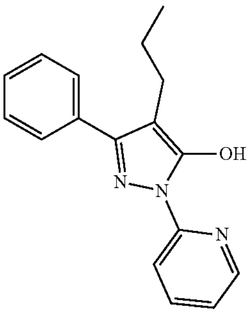 [SMILES: CCCc1c(-c2ccccc2)nn(-c2ccccn2)c1O]

2-Propyl-3-oxo-3-phenylpropionic acid ethyl ester (2.52 g, 10.7 mmol) and 10 ml of ethanol were placed in a round bottom flask, and then a solution of 2-hydrazinopyridine (1.29 g, 1.18 mmol) diluted in 3 ml of ethanol was slowly added dropwise thereto at 0° C. It was heated to reflux at 100° C. for 3 day. The solvent was removed by distillation under reduced pressure, and the resulting solid was washed with hexane and ethyl acetate, and then dried under vacuum to obtain the title compound in a yield of 82%.

1H NMR (300 MHz, $CDCl_3$) δ 12.50 (1H, s), 8.27-8.25 (1H, m), 8.01 (1H, d, J=8.5 Hz), 7.81 (1H, m), 7.69 (2H, m), 7.48-7.34 (3H, m), 7.12-7.10 (1H, m), 2.54 (2H, d, J=7.5

Hz), 1.64 (2H, m), 0.93 (3H, t, J=7.3 Hz); EIMS (70 eV) m/z (rel intensity) 279 (M+, 37), 250 (100)

<Synthetic Example 4> Synthesis of 3-phenyl-4-propyl-1-(pyridin-2-yl)-1H-pyrazol-5-ol hydrochloride (Compound 1)

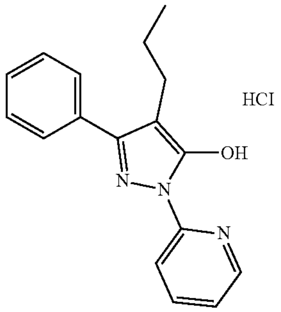

3-Phenyl-4-propyl-1-(pyridin-2-yl)-1H-pyrazol-5-ol (280 mg, 1.0 mmol) prepared in Synthetic Example 3 above was dissolved in 4 ml of ethyl ether in a round bottom flask, and then 0.55 ml of ethyl ether dissolved in 2 M HCl was slowly added dropwise thereto at 0° C. The solid produced from the reaction solution was filtered under reduced pressure, the solvent was removed, washed with hexane and ethyl acetate, and then dried under vacuum to obtain the title compound (270 mg, 0.85 mmol).

1H NMR (300 MHz, $CDCl_3$) δ 8.44 (1H, d, J=4.2 Hz), 8.0-8.03 (2H, m), 7.66-7.64 (2H, m), 7.48-7.42 (3H, m), 7.34-7.30 (1H, m), 2.49 (2H, brs), 2.43 (2H, t, J=7.5 Hz), 1.48 (2H, m), 0.48 (3H, t, J=7.3 Hz).

<Example 1> Analysis of Changes in Reactive Oxygen Species Generation in Normal Human Lung Fibroblasts In order to confirm the effect of the compounds of the synthetic examples on the generation of reactive oxygen species from lung fibroblasts, the generation of reactive oxygen species was induced through PMA stimulation in normal human lung fibroblasts (NHLFs, Lonza), and the inhibitory effect of Compound 1 on the generation of reactive oxygen species was observed under this condition.

Each cell was suspended in a culture medium containing 10% FBS, seeded in a 96-well plate, and cultured for 24 hours under conditions of 5% $CO_2$ and 37° C. After pre-treating Compound 1 for 30 minutes to 1 hour, TGF-β1 or phorbol 12-myristate 13-acetate (PMA) stimulation was applied to each well including cells and drugs. After additional culture for 30 minutes or 48 hours, the degree of generation of reactive oxygen species was confirmed using 8-amino-5-chloro-7-phenyl-2,3-dihydro-pyrido[3,4-d]pyridazine-1,4-dione (L-012) or 2',7'-dichlorodihydrofluoresencein diacetate (DCF-DA).

It was confirmed that the generation of PMA stimulation-induced reactive oxygen species was inhibited in a concentration-dependent manner when treated with Compound 1 (FIG. 1).

<Example 2> Expression Pattern of TGF-β1-Induced αSMA and Collagen Type I in Normal Human Lung Fibroblasts In order to analyze the effect of Compound 1 on the differentiation of lung fibroblasts into myofibroblasts, the inhibitory effect of Compound 1 on the increase in the expression of TGF-β1-induced α-smooth muscle actin (αSMA) and collagen type I (collagen I) in normal human lung fibroblasts (NHLFs, Lonza) was observed. NHLF cells were suspended in culture medium (FGM-2 Bulletkit media, Lonza) and inoculated at a concentration of $1\times10^4$ cells/well on a 4-well chamber slide (Nunc).

After 24 hours of culture in a $CO_2$ incubator, the medium was replaced with a serum-free medium and further cultured for 12 hours. Thereafter, vehicle and 2 mM Compound 1 were pre-treated in the corresponding wells for 1 hour, and then 10 ng/ml of TGF-β1 was treated in each well except for the negative control (vehicle group) for 72 hours.

Confirmation of the expression of αSMA and collagen I in the prepared cells was performed through immunocytochemistry as follows. Cells were fixed in 4% paraformaldehyde for 10 minutes and permeated using 0.1% Triton X-100, and primary antibody (anti-αSMA Ab, 1:200; anti-collagen I Ab, 1:500, reacted for 3 hours at room temperature) and secondary antibody (ALEXA™-594 conjugated Ab, 1:1000, reacted for 1 hour at room temperature) treatment process was sequentially performed, and then the expression of αSMA and collagen I was observed using a fluorescence microscope.

At this time, in order to quantitatively confirm the degree of expression of αSMA and collagen I, the number of DAPI (cell nuclear staining marker)-positive cells and αSMA- and collagen I-positive cells per each field was counted, respectively, and then the percentage of the number of αSMA- and collagen I-positive cells was calculated and compared using the following formula:

$$\%\ \alpha SMA\ (\text{or collagen } I)\text{–positive cells/field}$$

$$=\alpha SMA\ (\text{or collagen } I)\text{–positive cells}/DAPI\text{-positive cells}\times100/\text{field}$$

Figure 2:
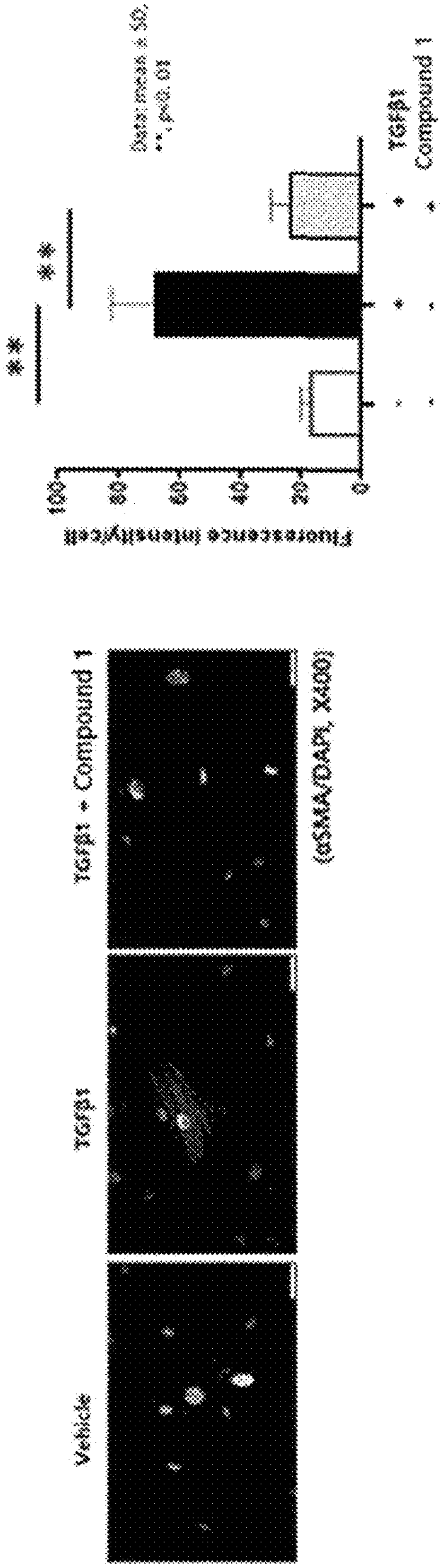
FIG. 2 shows the results of inhibiting the expression of αSMA by Compound 1 during the differentiation of normal human lung fibroblasts into myofibroblasts by TGF-β1.
Figure 3:
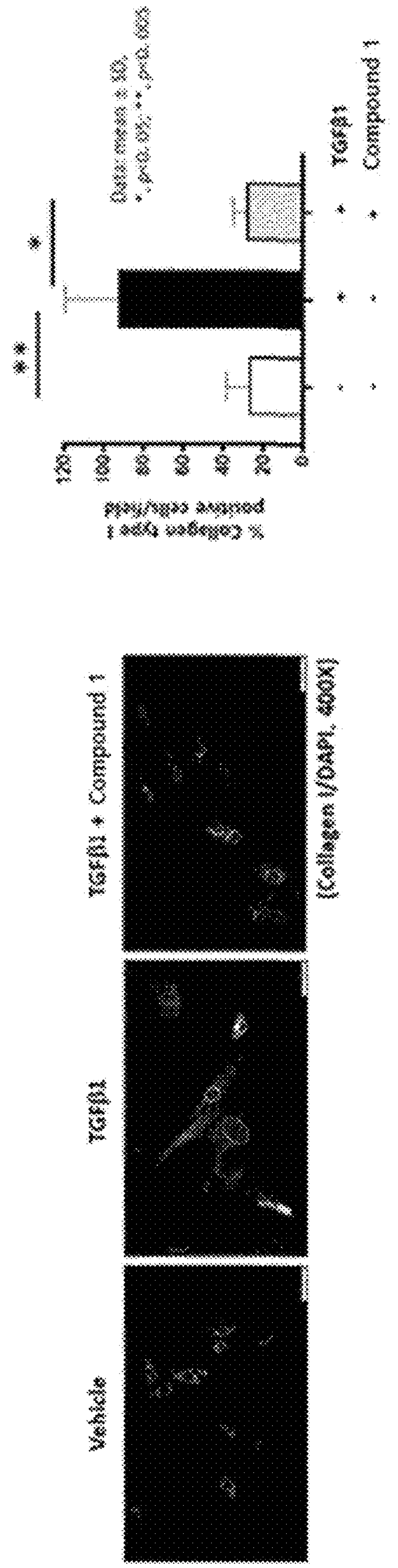
FIG. 3 shows the results of inhibiting the expression of collagen I by Compound 1 during the differentiation of normal human lung fibroblasts into myofibroblasts by TGF-β1.

As shown in FIGS. 2 and 3, it was observed that the expression of αSMA and collagen I was significantly increased compared to the control group when NHLFs were treated with 10 ng/ml TGF-β1, and the increase in the expression of both markers was remarkably inhibited when treated with Compound 1.

From these results, it was confirmed that Compound 1 could effectively inhibit the differentiation of lung fibroblasts into myofibroblasts induced by TGF-β1 treatment (see FIGS. 2 and 3).

<Example 3> Analysis of Changes in the Expression of LPS-Induced IL-1β

In order to confirm the effect of the compounds of the synthetic examples of the present invention on the inflammatory response in normal human lung fibroblasts (NHLFs, Lonza), whether the increased expression of IL-1β by LPS treatment was inhibited by Compound 1 was observed.

$2\times10^5$ cells were inoculated in a 6 well plate, cultured for 24 hours, and further cultured for 16 hours in a serum-free culture medium, and then Compound 1 was pre-treated for 30 minutes according to each condition and an inflammatory response was induced with LPS for 6 hours. IL-1β expression was confirmed using RT-PCR. Total RNA was isolated from cells using RNeasy mini kit (Qiagen), and cDNA was synthesized from 2 μg of the isolated RNA using PRIMESCRIPT™ II $1^{st}$ strand cDNA synthesis kit (TaKaRa), and then PCR was performed with ACCUPOWER® PCR PreMix (Bioneer) to amplify the gene. The base sequence for the target primer is as follows: IL-1β (forward: 5'-CCACA- GACCTTCCAGGAGAATG-3' (SEQ ID NO: 1), reverse: 5'-GTGCAGTTCAGTGATCGTACAGG-3' (SEQ ID NO: 2)); GAPDH (forward: 5'-GTGGCTGGCTCAGAAAAAGG-3' (SEQ ID NO: 3), reverse: 5'-GGTGGTCCAGGGGTCTTACT-3' (SEQ ID NO: 4)); β-actin (forward: 5'-CACCATTGGCAATGAGCGGTTC-3' (SEQ ID NO: 5), reverse: 5'-AGGTCTTTGCGGATGTCCACGT-3' (SEQ ID NO: 6). The PCR product was confirmed by electrophoresis on 1.5% agarose gel.

Figure 4:
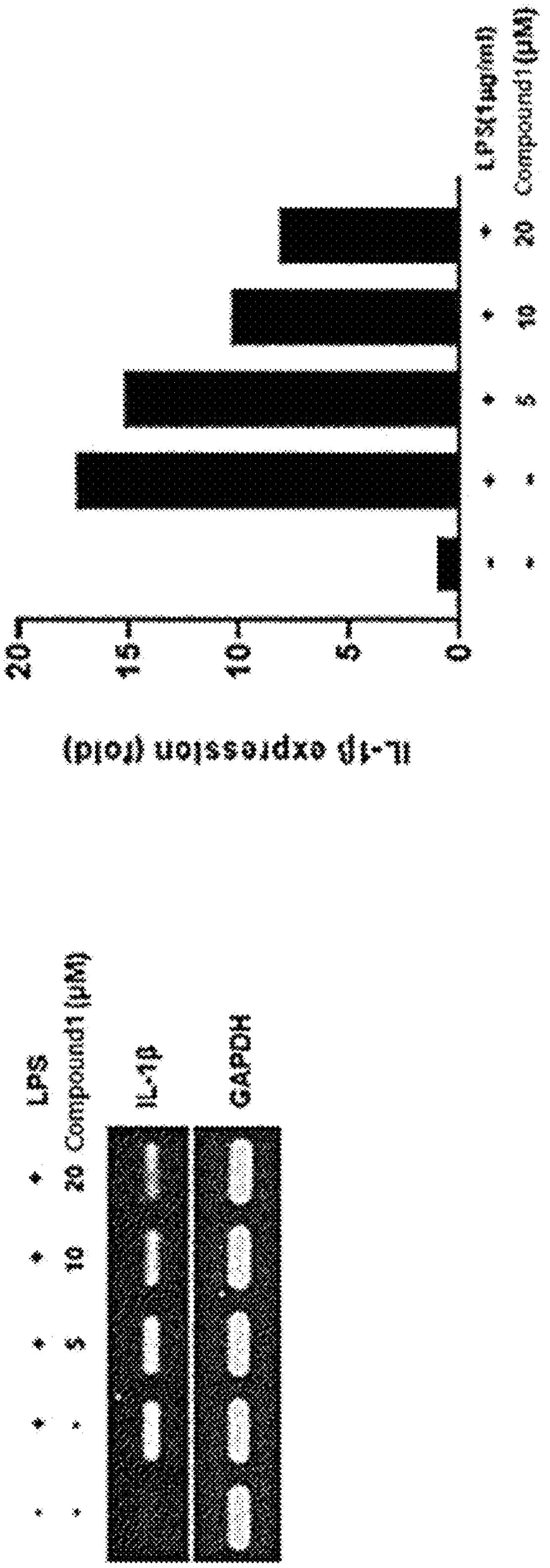
FIG. 4 shows the result of effectively inhibiting the expression of LPS treatment-induced IL-1β in normal human lung fibroblasts when treated with Compound 1.

As a result of the experiment, as can be seen in FIG. 4, it was observed that LPS-induced IL-1β was effectively inhibited in a concentration-dependent manner when treated with Compound 1 (see FIG. 4).

<Example 4> Confirmation of Therapeutic Effect on Pulmonary Fibrosis in a Mouse Model with Bleomycin-Induced Pulmonary Fibrosis For the mouse model with bleomycin-induced pulmonary fibrosis, C57BL/6J male mice aged 5 weeks and before and after body weight of 20 g were used. C57BL/6J mice were anesthetized by intraperitoneally injection of pentobarbital (40 mg/kg), the skin of the anterior neck or midline was incised, the trachea was exposed with a self-retaining retractor, and then a micro syringe was inserted from the occipital side to the lungs to slowly administer bleomycin (2 mg/kg) while checking the state of respiration. Immediately after injection, the skin of the incised anterior neck or midline was sutured, and then they were bred in a sterile animal room at constant temperature (22-26° C.) and constant humidity (55-60%). By this method, remarkable fibrosis occurred in the lungs, usually after 3 weeks of treatment.

Experimental animals were 7 animals in each group, and the experiment was conducted by dividing them into the following groups: a control group (Control) orally administered with distilled water, a group (BLM) with bleomycin-induced pulmonary fibrosis, an experimental group as a positive control group (BLM+Nintedanib) orally administered with 100 mg/kg of nintedanib daily 3 weeks after administration of bleomycin, and an experimental group (BLM+Compound 1) orally administered with 60 mg/kg of Compound 1 daily 3 weeks after administration of bleomycin.

Nintedanib and Compound 1 were orally administered once a day for 28 days. On the day after the last administration of nintedanib or compound 1, each animal was anesthetized, and then was bled by cardiac puncture and sacrificed.

Lung tissues were enucleated from all animals for histopathological examination. The enucleated lung tissue was fixed in 10% neutral buffered formalin (NBF). The fixed lung tissue was embedded in paraffin and sliced to a thickness of 4 μm to prepare a tissue slide.

The tissue slides were subjected to hematoxylin & eosin (H&E) staining, which is cell staining, and Masson's trichrome (MT) staining to confirm fibrosis. Histopathological examination of the prepared tissue slides was confirmed using an optical microscope (Carl Zeiss, Oberkochen, Germany). The severity of fibrosis was assessed using the modified Ashcroft scale, which is a semi-quantitative histopathological scoring.

For immunohistochemical staining, the tissue slides prepared above were de-paraffinized, and then rabbit anti-α-smooth muscle actin (SMA) antibody or rabbit anti-collagen type I antibody was used as a primary antibody. And, Vectastatin ABC kit (Vector Laboratories, Inc, Burlingame, CA) was used to confirm the expression of the antigen reacted with each antibody.

After reacting for 5 minutes using 3,3'-diaminobenzidine (DAB) as a substrate for peroxidase, it was observed under a 400 magnification field of view with an optical microscope. When reading the staining result, if the cytoplasm is colored reddish-brown in whole or in part, it is considered that there is an immune reaction, and thus, it is read as positive.

From the experimental results, the mean and standard deviation were obtained using the SPSS ver. 22.0 statistical program (SPSS Inc., Chicago, IL, USA), and the significance of the difference between the experimental groups was verified at $p<0.05$ level by the student t-test.

Figure 5:
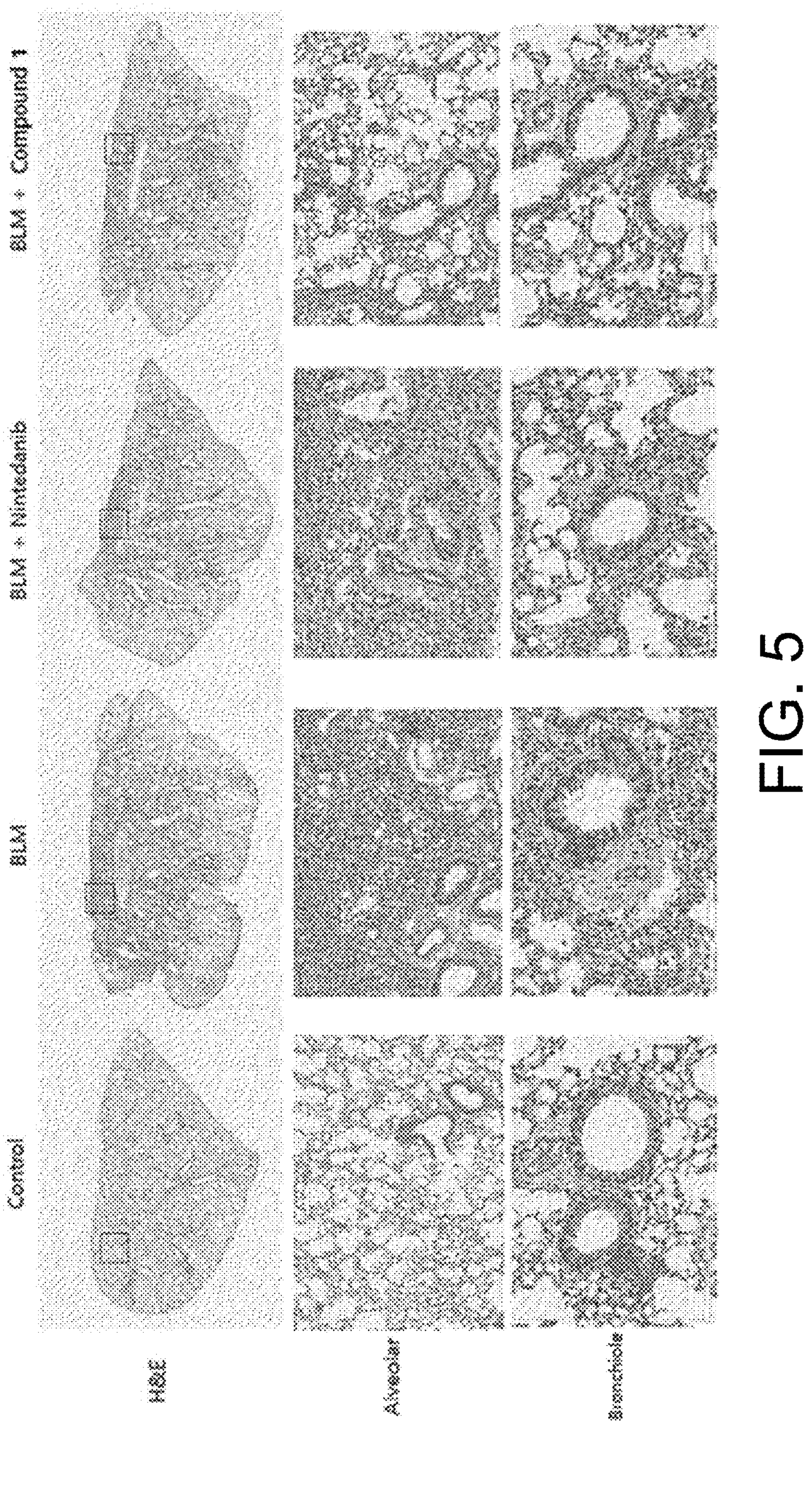
FIG. 5 is photographs showing H&E staining of alveolus and bronchiole when treated with nintedanib or Compound 1 in an animal model with bleomycin administration-induced pulmonary fibrosis (BLM), and shows the result of reducing the amount of immune cells penetrating into the alveolus and bronchiole when treated Compound 1.

As a result of histological analysis through H&E staining, among an experimental group (BLM) with bleomycin-induced lung fibrosis, a positive control group (BLM+Nintedanib) administered with nintedanib, and a group administered with Compound 1 (BLM+Compound 1), it was confirmed that in the group administered with Compound 1 (BLM+Compound 1), the degree of infiltration of inflammatory cells into the alveolus and bronchiole was significantly lower than that of the experimental group and the positive control group. In addition, it was confirmed that the hypertrophic epithelial cells were decreased, the deformation of the lung structure was reduced, and the site of abnormal tissue deposition was reduced (see FIG. 5).

Figure 6:
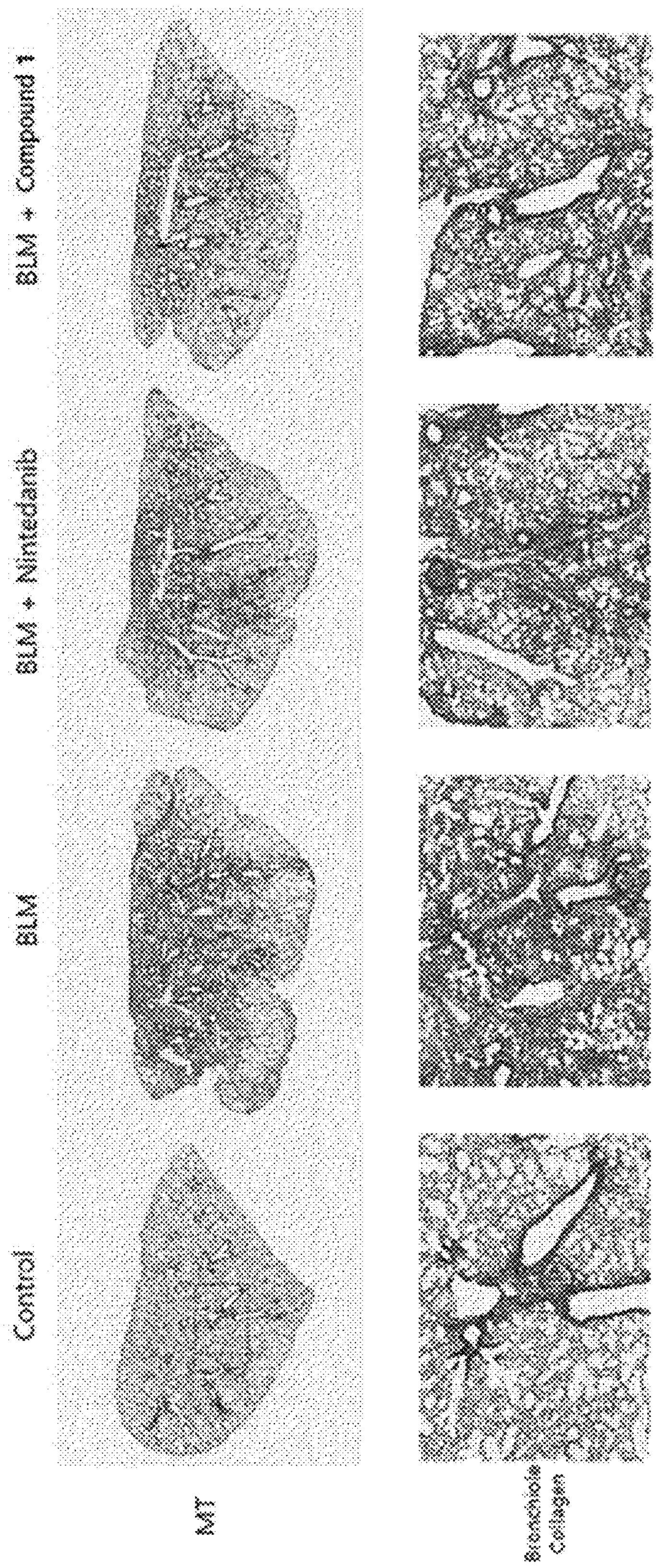
FIG. 6 is photographs showing collagen deposition staining of bronchiole when treated with nintedanib or Compound 1 in an animal model with bleomycin administration-induced pulmonary fibrosis (BLM), and shows the result of reducing collagen deposition when treated Compound 1.

In FIG. 6, the degree of lung fibrosis in the group administered with Compound 1 (BLM+Compound 1) was analyzed compared to those of the experimental group with bleomycin-induced pulmonary fibrosis (BLM) and the positive control group administered with nintedanib (BLM+Nintedanib) through Masson's trichrome (MT) staining method specific for lung fibrosis. As a result, it was confirmed that the size of the fibrosis area and the deposition of collagen due to fibrosis were remarkably reduced in the group administered with Compound 1 (BLM+Compound 1) compared to the experimental group and the positive control group.

Figure 7:
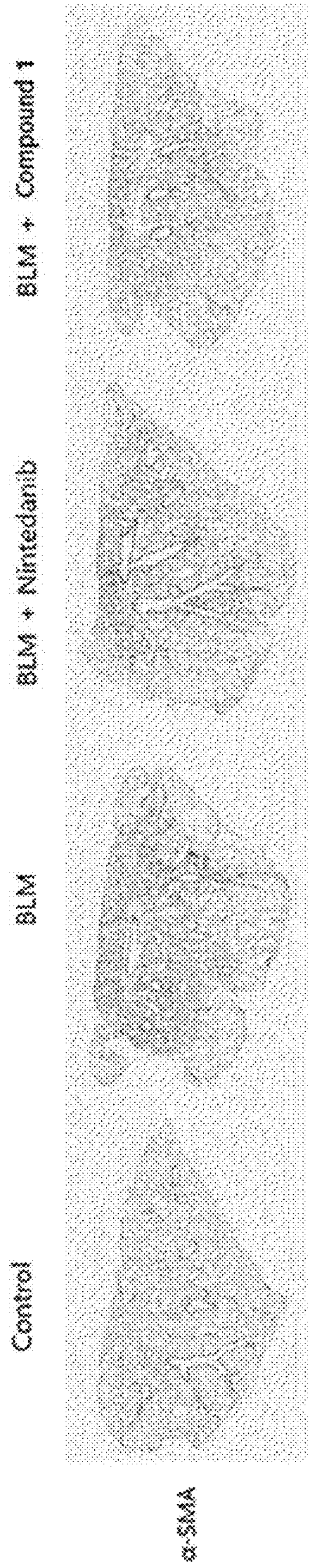
FIG. 7 is photographs showing the staining of αSMA when treated with nintedanib or Compound 1 in an animal model with bleomycin administration-induced pulmonary fibrosis (BLM), and shows a decrease in the expression of αSMA when treated Compound 1.
Figure 8:
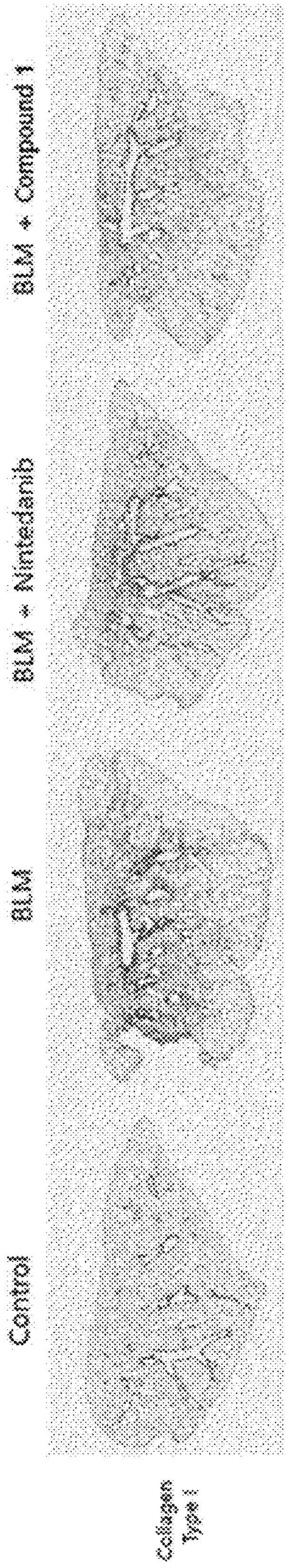
FIG. 8 is photographs showing the staining of collagen I when treated with nintedanib or Compound 1 in an animal model with bleomycin administration-induced pulmonary fibrosis (BLM), and shows a decrease in the expression of collagen I when treated Compound 1.

In FIGS. 7 and 8, it may be conformed that the expression of α-SMA was reduced in the group administered with Compound 1 (BLM+Compound 1) compared to the experimental group with bleomycin-induced pulmonary fibrosis (BLM) and the positive control group administered with nintedanib (BLM+Nintedanib) (FIG. 7), and it was conformed that the expression of collagen type I (collagen I) was also remarkably reduced in the group administered with Compound 1 (BLM+Compound 1) compared to the experimental group (BLM) and the positive control group (BLM+Nintedanib) (FIG. 8).

Comprehensively, after quantifying the histological and immunological results with the modified Ashcroft scale widely used in the field of lung fibrosis histology, the severity of pulmonary fibrosis in the group administered with Compound 1 (BLM+Compound 1) was evaluated compared to those of the negative control group (Control), the experimental group (BLM) and the positive control group (BLM+Nintedanib), respectively.

Figure 9:
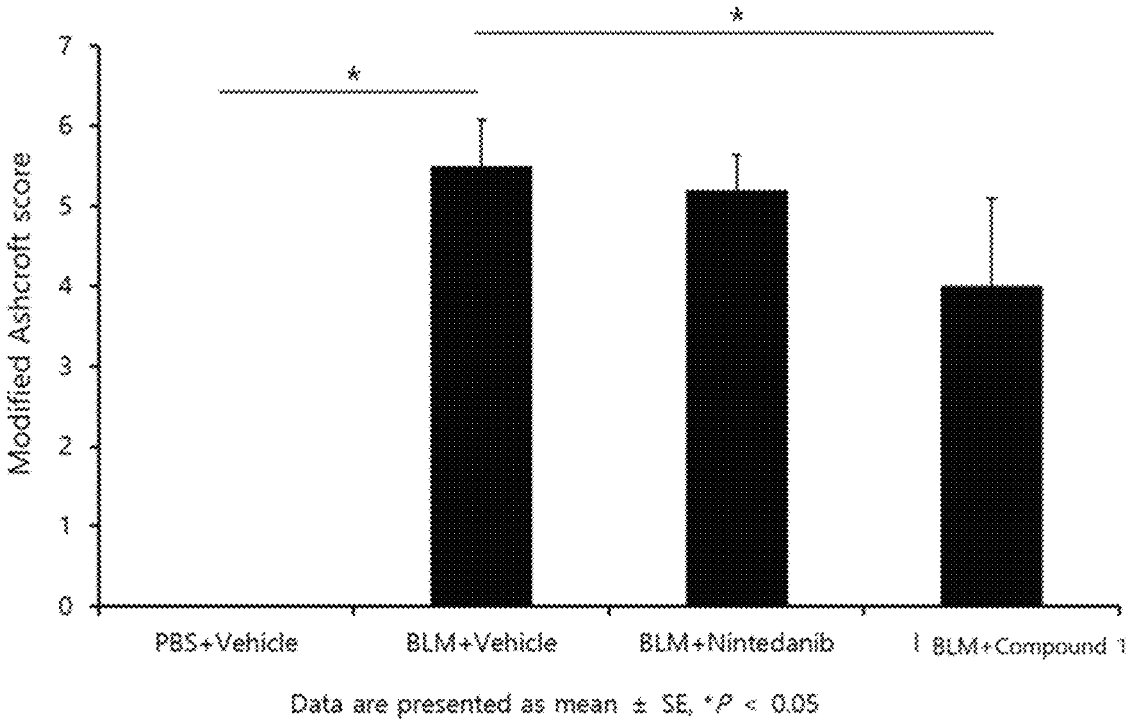
FIG. 9 is the result of quantifying the degree of lung fibrosis with the improved Ashcroft scale when treated with nintedanib or Compound 1 in an animal model with bleomycin administration-induced pulmonary fibrosis (BLM), and shows effective improvement of pulmonary fibrosis compared to nintedanib when treated with compound 1.

As shown in FIG. 9, the score was 0 in the negative control group (PBS) showing normal findings, and the score was 5.5±0.8 in the experimental group (BLM) with bleomycin-induced pulmonary fibrosis. The improved Ashcroft score of the positive control group administered with nintedanib (BLM+Nintedanib) was reduced to 5.2±0.45, and the improved Ashcroft score of the experimental group administered with Compound 1 (BLM+Compound 1) was 4.0±1.1, and thus, it was confirmed that the compound of the present invention effectively improved pulmonary fibrosis compared to nintedanib, which has been used as a conventional therapeutic agent for idiopathic pulmonary fibrosis.

<Example 5> Confirmation of Virus Inhibitory Effect in Human Lung Epithelial Cells In order to analyze the antiviral activity of the compounds of the synthetic examples, real-time qRT-PCR (quantitative RT-PCR) was perfumed using severe acute respiratory syndrome coronavirus 2 (SARS-CoV2) and Calu-3 cells, which are human lung epithelial cells. Human lung epithelial cells (Calu-3) were cultured in Dulbecco's Modified Eagle Medium (DMEM) at 37° C. under 5% $CO_2$. The concentration of Compound 1 was 15, 12.5, 6.25, 3.125, 1.563, 0.781, 0.391, 0.195, 0.098, 0.049, 0.024, 0.012 μM. Antiviral efficacy ($IC_{50}$; 50% inhibition concentration) and toxicity to the cells ($CC_{50}$; 50% cytotoxic concentration) according to drug concentration were measured at 24 hours and 48 hours after treatment on the cells by concentration, and are shown in Table 1 and FIG. 10.

TABLE 1

| Time (h) | $CC_{50}$ | $IC_{50}$ | SI |
|---|---|---|---|
| 24 | 435 | 31.53 | 13.80 |
| 48 | 164.5 | 1.67 | 98.50 |

Figure 10:
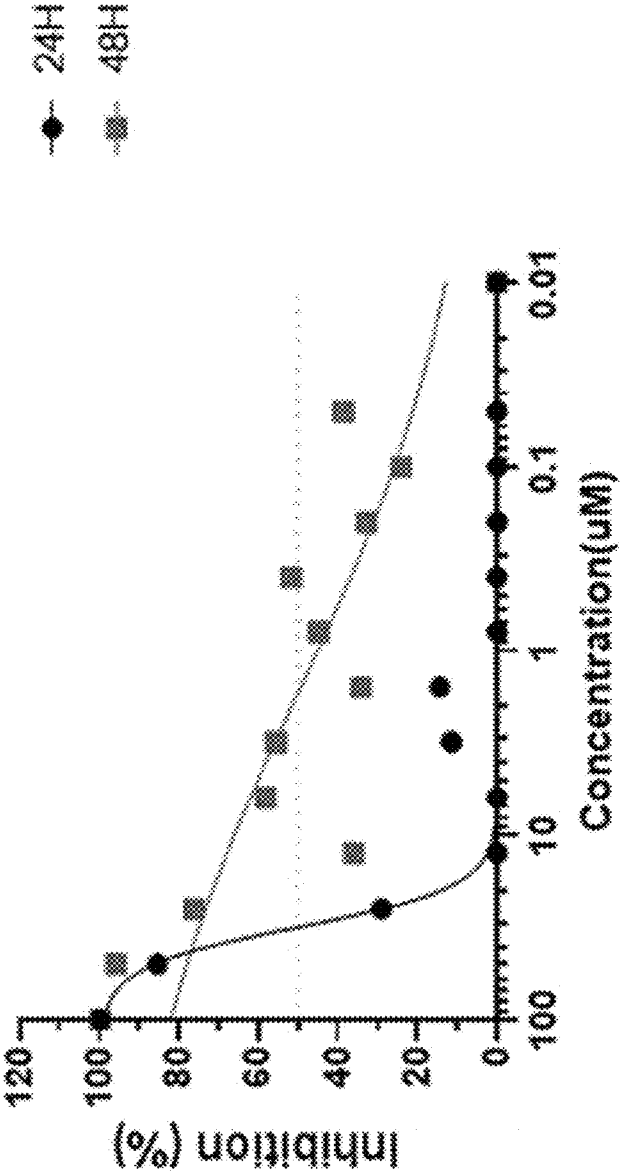
FIG. 10 shows that the antiviral efficacy is excellent and the cytotoxicity is low, when treated with Compound 1 in human lung epithelial cells.

As can be seen from Table 1 and FIG. 10, the antiviral efficacy showed an $IC_{50}$ of 1.67 μM at 48 hours, and the cytotoxicity showed a very low cytotoxicity as a $CC_{50}$ of 164.5 μM at 48 hours. Therefore, it was confirmed that Compound 1 could inhibit the replication of SARS-CoV-2 and was a drug having very low cytotoxicity.

The invention claimed is:

1. A method of treating virus-induced pulmonary fibrosis in a mammal in need thereof, comprising administering an effective amount of a compound of following Formula 1 or a pharmaceutically acceptable salt thereof to the mammal:

Formula 1

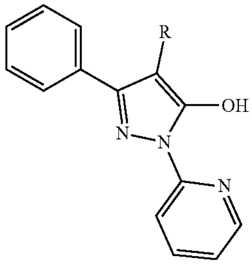

wherein R is a linear or branched alkyl group having 1 to 6 carbon atoms, and wherein the compound of Formula 1 is used together with an antiviral agent.

2. The method according to claim 1, wherein the compound of Formula 1 is:

3-phenyl-4-methyl-1-(pyridin-2-yl)-1H-pyrazol-5-ol or a hydrochloride salt thereof;

3-phenyl-4-ethyl-1-(pyridin-2-yl)-1H-pyrazol-5-ol or a hydrochloride salt thereof, 3-phenyl-4-n-propyl-1-(pyridin-2-yl)-1H-pyrazol-5-ol or a hydrochloride salt thereof, 3-phenyl-4-isopropyl-1-(pyridin-2-yl)-1H-pyrazol-5-ol or a hydrochloride salt thereof, 3-phenyl-4-n-butyl-1-(pyridin-2-yl)-1H-pyrazol-5-ol or a hydrochloride salt thereof, 3-phenyl-4-tert-butyl-1-(pyridin-2-yl)-1H-pyrazol-5-ol or a hydrochloride salt thereof, 3-phenyl-4-n-pentyl-1-(pyridin-2-yl)-1H-pyrazol-5-ol or a hydrochloride salt thereof, or 3-phenyl-4-n-hexyl-1-(pyridin-2-yl)-1H-pyrazol-5-ol or a hydrochloride salt thereof.

3. The method according to claim 2, wherein the compound of Formula 1 is 3-phenyl-4-n-propyl-1-(pyridin-2-yl)-1H-pyrazol-5-ol or a hydrochloride salt thereof.

4. The method according to claim 1, wherein the pulmonary fibrosis is caused by pulmonary inflammatory fibrosis, chronic obstructive pulmonary disease (COPD) combined pulmonary fibrosis, idiopathic pulmonary fibrosis (IPF) or asthma.

5. The method according to claim 4, wherein the pulmonary inflammatory fibrosis is caused by any one or combination of viral pneumonia, bacterial pneumonia, fungal pneumonia, mycoplasmal pneumonia, hypersensitivity pneumonitis, aspiration pneumonia, interstitial pulmonary disease, and pneumoconiosis.

6. The method according to claim 5, wherein the viral pneumonia is caused by a virus selected from adenovirus, vaccinia virus, herpes simplex virus, parainfluenza virus, rhinovirus, varicella zoster virus, measles virus, respiratory syncytial virus, dengue virus, human immunodeficiency virus (HIV), influenza virus, coronavirus, severe acute respiratory syndrome-related coronavirus 2 (SARS-CoV2), middle east respiratory syndrome coronavirus (MERS-CoV), or variant viruses of these viruses.

7. The method according to claim 4, wherein the pulmonary fibrosis is caused by idiopathic pulmonary fibrosis.

8. The method according to claim 1, wherein the method further comprises administering a pharmaceutically acceptable carrier or excipient to the mammal.

9. The method according to claim 1, wherein the compound of Formula 1 is used further together with a second therapeutic agent, wherein the second therapeutic agent is an antibiotic, an antifungal agent, an anti-inflammatory agent, or any combination thereof.

* * * * *